United States Patent [19]
Karhu

[11] Patent Number: 5,578,771
[45] Date of Patent: Nov. 26, 1996

[54] METHOD FOR MEASURING PARTICLE SIZE DISTRIBUTION

[75] Inventor: Lauri Karhu, Espoo, Finland

[73] Assignee: Outokumpu Mintec OY, Espoo, Finland

[21] Appl. No.: 563,133

[22] Filed: Nov. 27, 1995

Related U.S. Application Data

[63] Continuation-in-part of Ser. No. 196,005, Feb. 9, 1994, abandoned.

[30] Foreign Application Priority Data

Feb. 12, 1993 [FI] Finland ..................................... 930617

[51] Int. Cl.$^6$ ............................................. G01N 15/02
[52] U.S. Cl. .................................................. 73/865.5
[58] Field of Search ........................... 73/865.5; 364/555

[56] References Cited

U.S. PATENT DOCUMENTS

| | | | |
|---|---|---|---|
| 3,662,884 | 5/1972 | Robinson | 209/129 |
| 3,873,206 | 3/1975 | Wilcock | 356/338 |
| 4,554,051 | 11/1985 | Danforth | 73/53.04 X |
| 4,684,069 | 8/1987 | Hashimoto et al. | 241/79.1 |
| 5,311,783 | 5/1994 | Takeuchi | 73/865.5 |
| 5,359,907 | 11/1994 | Baker et al. | 73/865.5 |

FOREIGN PATENT DOCUMENTS

| | | |
|---|---|---|
| 903351 | 1/1992 | Finland . |
| 542124 | 4/1977 | U.S.S.R. . |
| 823982 | 4/1981 | U.S.S.R. . |
| 1452458 | 10/1976 | United Kingdom . |

*Primary Examiner*—Thomas P. Noland
*Attorney, Agent, or Firm*—Smith-Hill and Bedell

[57] ABSTRACT

Particle size distribution of a flowing material that is composed of solid particles in a carrier fluid is measured employing a measuring element that comprises first and second measuring members having respective confronting measuring surfaces of predetermined area and a mechanism for causing relative movement of the measuring members toward and away from each other. The area of each measuring surface is at least 0.008–0.5 cm$^2$ per percent solids of the flowing material.

13 Claims, 1 Drawing Sheet

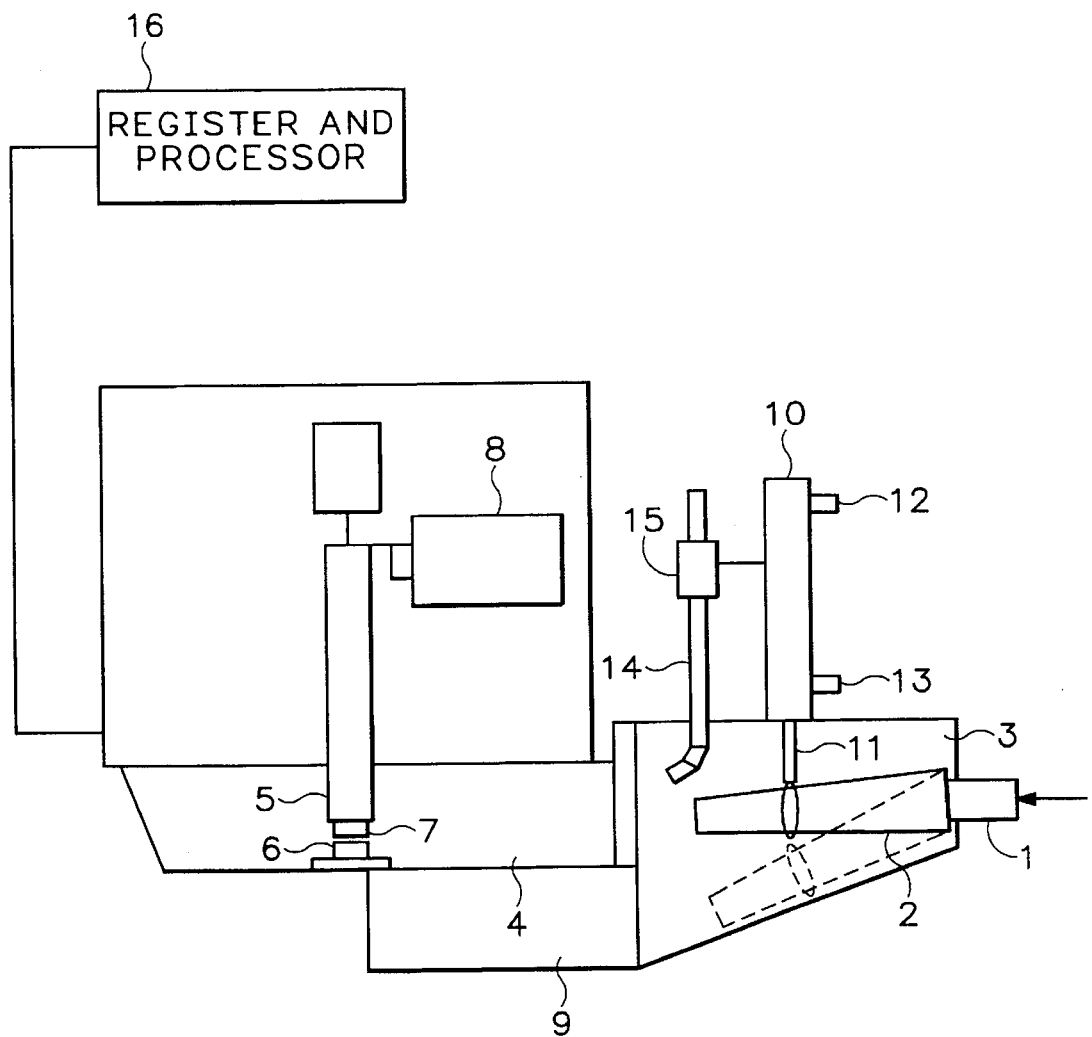

METHOD FOR MEASURING PARTICLE SIZE DISTRIBUTION

CROSS-REFERENCE TO RELATED APPLICATION

This application is filed as a continuation-in-part of U.S. patent application No. 08/196,005 filed Feb. 9, 1994 and now abandoned.

BACKGROUND OF THE INVENTION

The present invention relates to a method for measuring particle size distribution of a flowing material that comprises solid particles in a carrier fluid, which may be liquid and/or gas.

Finnish patent application No. 903351 discloses a method for measuring particle size distribution of a bulk material, employing a particle size detector that comprises a stationary measurement member and a movable measurement member that is displaced cyclically back and forth in relation to the stationary measurement member. As the movable measurement member moves toward the stationary measurement member, a sample of the flowing material is captured between the measurement members and interferes with movement of the movable measurement member, and the minimum distance of the movable measurement member from the stationary measurement member is representative of the size of the particles in the sample. When the movable measurement member is displaced away from the stationary measurement member, the sample is no longer trapped between the measurement members and the bulk material flows between the measurement members. During the next cycle of movement, the movement of the movable measurement member toward the stationary measurement member might be interrupted by a sample containing particles that are larger or smaller than those of the sample which interrupted its movement on the previous cycle. By recording the minimum distance of the movable measurement member from the stationary measurement member on each cycle of movement, information regarding the particle size distribution in the bulk material is obtained.

From time to time it is necessary to wash the particle size detector, particularly the measurement members, in order to remove residues of the bulk material that remain on the measuring members and affect subsequent measurements. For this purpose, the particle size detector is located in a measuring channel and a by-pass channel is connected in parallel with the measuring channel. A bulk material feeding pipe is connected to a deflectable nozzle for guiding the bulk material flow either to the measuring channel or to the by-pass channel. The nozzle directs the flow of the bulk material under measurement to the measuring channel when the particle size distribution is being measured and to the by-pass channel when the measuring channel is being washed.

A control chamber is divided into two compartments by means of a displaceable actuator provided in the control chamber, and the displaceable actuator is connected to the deflectable nozzle by means of a spring-loaded coupling rod. One of the compartments of the chamber is connected to a washing water feed pipe for feeding washing water to the measuring channel. When the particle size detector is to be washed, a valve that connects the washing water feed pipe to a supply of water under pressure is opened. The pressure of the water supply is communicated to the control chamber, so that the displaceable actuator and the coupling rod are displaced against the resistance of the spring and the nozzle is deflected. The bulk material flow is directed to the by-pass channel instead of the measuring channel. Further, washing water is supplied to the measuring channel for cleaning the particle size detector. In order to interrupt the washing of the particle size detector, the valve of the washing water feed pipe is closed. The spring returns the displaceable actuator to its previous position and the nozzle again directs the bulk material flow to the measuring channel.

According to Finnish patent application No. 903351, the same particle size detector is used for both coarse and fine particles, which means that the detector is easily susceptible to mechanical wear. Likewise, the measuring accuracy of the particle size detector is reduced by the fact that the same detector is used for materials with different solid contents.

SUMMARY OF THE INVENTION

The object of the present invention is to eliminate some of the drawbacks of the prior art and to achieve an improved and operationally more secure method, wherein the measuring accuracy of the particle size detector is advantageously improved by utilizing measuring members of which the measuring area is dependent on the solid content of the material under measurement. The essential novel features of the invention are apparent from the appended patent claims.

In accordance with the method of the invention, the material under measurement is conducted through a feed pipe into a measuring channel, where a measuring element for defining the particle size of the material is installed. The measuring element is composed of two measuring members, one of which remains stationary and the other moves cyclically back and forth in relation to the stationary measuring member. Some of the material flowing through the measuring channel passes between the confronting surfaces of the measuring members and when the movable measuring member moves toward the stationary measuring member, a sample of the flowing material is captured between the measuring members and interferes with movement of the movable measuring member toward the stationary measuring member. On each cycle of movement of the measuring members, the minimum distance of the movable measuring member from the stationary measuring member is measured and recorded. The particle size values obtained from the measuring element are electrically transferred to a registering device, which further translates the obtained values to particle size distribution.

It has now been recognized, according to the invention, that for a given pair of measuring members, the size of the random sample that is captured between the measuring members when the measuring members are moved together, and hence the quantity of particles used in determining the particle size distribution, depends on the solid content of the flowing material.

According to the invention, the measuring area of the measuring members in the measuring channel advantageously depends on the solid content of the material under measurement. In particular, according to the invention, the measuring area of the measuring members is advantageously maintained such that irrespective of the solid content of the material under measurement, the random sample that is captured by the measuring element and used for determining the particle size distribution will be essentially constant in volume. The size of the random sample can advantageously be controlled by means of the ratio of the measuring area and the solid content. According to the invention, the ratio of the measuring area and the solid content is within the range 0.008–0.5, advantageously 0.015–0.025 square centimeter per percent solids. The solid content of the flowing material that is measuredly the method according to the invention can fluctuate from 1 to 60 percent.

In practicing the method of the invention, the registering device can be implemented such that it gives as a measurement result one or more parameters representing the particle size distribution of the material to be measured. Such parameters are for instance the mass fraction of one predetermined particle size class or the particle size of one predetermined mass fraction. The determination of these parameters is based on the average and the standard deviation of the consecutive measurements recorded in the registering device. The parameters based on the measurements are reliable because the fluctuations in the solid content can be compensated when the ratio of the measuring area and the solid content does not vary widely.

The method of the invention can be applied to a flowing material, wherein the carrier fluid is a liquid or a gas or a combination thereof. The material under measurement can be a slurry-like material, where the carrier fluid is a liquid, usually water. In addition to this, the method of the invention can be used for measuring solid substances that are fluidized, for instance by a gas, such as air.

Residues of particles of the material under measurement may remain on the measuring surfaces during the particle size distribution measurements, and such residues may degrade the measuring accuracy of the particle size detector. Particle residues can be cleaned from the measuring surfaces with a cleaning medium, which can be a liquid, such as water, or a gas, such as air. Advantageously the cleaning medium is liquid if the carrier fluid is liquid. Likewise, when the carrier fluid is gas, the cleaning medium advantageously is gas, too. In order to carry out the cleaning, the material under measurement is directed through a by-pass channel, connected in parallel with the measuring channel for the duration of the cleaning operation. When the cleaning operation is to start, the actuators used in the cleaning are activated. Owing to the activation of the actuators, the connected valve system shifts a material flow guide member so that the material flow is directed into the by-pass channel instead of the measuring channel. Simultaneously the valve system opens the valve that supplies the cleaning medium, and the cleaning medium starts to flow into the measuring channel. After the cleaning operation, the valve system first interrupts the flow of the cleaning medium, and thereafter shifts the deflectable nozzle to direct the material flow back into the measuring channel. The method of the invention is then advantageously returned to the operational stage, i.e. to the determination of particle size distribution.

BRIEF DESCRIPTION OF THE DRAWINGS

The invention is explained in more detail below, with reference to the appended drawing, which illustrates in partial cross-section, viewed from the side, apparatus for carrying out a preferred embodiment of the invention.

DETAILED DESCRIPTION

The material under measurement is fed through a feeding conduit 1 to a feeding nozzle 2, which is located in a feeding chamber 3 and is turnably connected to the feeding conduit 1. When the apparatus is in operation in order to determine the particle size distribution of the material under measurement, such as a slurry flow, the material is directed by the feeding nozzle 2 to a measuring channel 4. A measuring element 5 composed of two measuring members 6 and 7 having confronting parallel surfaces is installed in the measuring channel. The first measuring member 6 is installed in a stationary fashion in the measuring channel 4. The second measuring member 7 is connected to a drive mechanism 8 located outside the measuring channel 4, which drive mechanism 8 causes the measuring member 7 to move toward the second member 6 and away therefrom at a desired frequency. Advantageously the measuring members 6 and 7 are made of durable material, such as silicon carbide. Each measuring member has a planar measuring surface that confronts the measuring surface of the other measuring member and is perpendicular to the direction of movement of the member 7. Moreover, the measuring area of the measuring members 6 and 7 advantageously is proportional to the solid content of the material under measurement.

The measuring members 6 and 7 of the measuring element are advantageously operated in relation to each other according to the micrometer principle, as described above in connection with Finnish Patent Application No. 903351. The measuring members 6 and 7 are located in the measuring channel 4 so that at least some of the solid particles contained in the flowing material under measurement pass in between the measuring members 6 and 7. Now, when the measuring member 7 moves back and forth in relation to the measuring member 6, from the particle or particles remaining between the measuring members 6 and 7, there is measured, according to the micrometer principle, the dimension essentially perpendicular to the measuring surfaces of the measuring members 6 and 7. The result is electrically transferred to the registering and processing device 16 that is connected to the measuring device, so that the particle size distribution of the material under measurement can be defined as a combination of several different measuring results.

Because the measuring members 6 and 7 are at least partly in physical contact with the solid particles under measurement during measurement operation, there arises from time to time a need to clean the measuring members 6 and 7 of the solid particle residues that possibly remain thereon in order to maintain the measuring accuracy of the apparatus. A cleaning medium, such as water, can be conducted into the measuring channel 4 through a conduit 14 that is controlled by an electrically operated valve 15. In order to start the cleaning operation, actuators required in the cleaning of the apparatus are activated. First, in order to change the route of the material flow from the measuring channel 4 to the by-pass channel 9, the position of the material feeding nozzle 2 is changed by using the guide member 10. The feeding nozzle 2 is connected, by means of a connecting member 11, to the guide member 10 and the position of the feeding nozzle 2 is adjusted for the cleaning operation by means of compressed air conducted into the ports 12 and 13 of this guide member under control of a valve (not shown). The guide member 10 is further electrically connected to the valve 15. When the feeding nozzle 2 is positioned so that the material flow is conducted into the by-pass channel 9, the valve 15 connected to the conduit 14 is opened, and the cleaning medium flows freely into the measuring channel and further onto the measuring members 6 and 7 for cleaning the measuring members. At the end of the cleaning operation, first the valve 15 provided in the conduit 14 is closed and then the feeding nozzle 2 is returned to the position where the material flow can enter the measuring channel 4.

Generally, the flowing material from a given source is fairly homogeneous and so the solid content of the flowing material taken from that source does not vary widely with time. In the event that the source of the flowing material is changed and the flowing material from the new source has a quite different solid content from before, the measuring members 6 and 7 are replaced. In each case, the measuring members are selected such that if the flowing material has a low solid content, the area of the measuring surfaces is larger, and conversely when the flowing material has a high solid content, the area of the measuring surfaces is smaller. By selecting the area of the measuring surfaces such that the ratio of the area of the measuring surfaces to the solid content does not vary widely, the size of the random sample that is taken when the measuring members reach their minimum distance apart remains within a narrow range. The measuring result obtained with flowing materials from different sources can then be compared with a higher degree of validity than if the size of the random samples varied substantially.

The above description illustrates the invention with reference to one preferred embodiment only, but the invention can be largely modified within the scope of the appended patent claims.

I claim:

1. A method of measuring particle size distribution of a flowing material that is composed of solid particles in a carrier fluid and has a known percent solids, the method employing a measuring element that comprises first and second measuring members having respective confronting measuring surfaces and a means for causing relative movement of the measuring members toward and away from each other, and wherein the area of one of said measuring surfaces is in the range 0.008–0.5 $cm^2$ divided by said known percent solids and the area of the other of said measuring surfaces is at least as great as that of said one measuring surface.

2. A method according to claim 1, wherein the measuring element is disposed in a measuring channel and the method further comprises:

supplying the flowing material to the measuring channel, discontinuing supply of the flowing material to the measuring channel and diverting supply of flowing material to a by-pass channel that by-passes the measuring channel, supplying cleaning fluid to the measuring channel for cleaning the measuring surfaces of the measuring members, discontinuing supply of cleaning fluid to the measuring channel, and restoring supply of the flowing material to the measuring channel.

3. A method according to claim 2, wherein the carrier fluid is a liquid.

4. A method according to claim 3, wherein the cleaning fluid is a liquid.

5. A method according to claim 2, wherein the carrier fluid is a gas.

6. A method according to claim 5, wherein the cleaning fluid is a gas.

7. A method according to claim 2, wherein the cleaning fluid is a liquid.

8. A method according to claim 2, wherein the cleaning fluid is a gas.

9. A method according to claim 1, wherein the solid content is in the range from about 1 percent to about 60 percent of the flowing material.

10. A method according to claim 1, wherein the area of each of said measuring surfaces is in the range from about 0.015 to about 0.025 $cm^2$ divided by said known percent solids.

11. A method according to claim 1, wherein the carrier fluid is a liquid.

12. A method according to claim 1, wherein the carrier fluid is a gas.

13. A method according to claim 1, comprising recording average particle size and standard deviation in particle size.

* * * * *